US008939882B2

(12) United States Patent
Reichenbach et al.

(10) Patent No.: US 8,939,882 B2
(45) Date of Patent: Jan. 27, 2015

(54) MULTI-LUMEN CANNULA

(75) Inventors: Steven H. Reichenbach, Pleasanton, CA (US); Yu Fai Law, Daly City, CA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/561,197

(22) Filed: Jul. 30, 2012

(65) Prior Publication Data
US 2012/0296152 A1 Nov. 22, 2012

Related U.S. Application Data

(63) Continuation of application No. 12/469,328, filed on May 20, 2009, now Pat. No. 8,231,519.

(51) Int. Cl.
| A61N 1/372 | (2006.01) |
| A61M 1/36 | (2006.01) |
| A61M 25/00 | (2006.01) |
| A61M 1/10 | (2006.01) |

(52) U.S. Cl.
CPC ......... *A61M 1/3653* (2013.01); *A61M 25/0032* (2013.01); *A61M 1/1008* (2013.01); *A61M 1/3659* (2013.01); *A61M 25/0023* (2013.01); *A61M 2025/0035* (2013.01)
USPC .......................................... 600/16; 604/4.01

(58) Field of Classification Search
USPC ..................... 600/16; 604/4.01, 6.11; 623/3.1
See application file for complete search history.

(56) References Cited

U.S. PATENT DOCUMENTS

| 4,619,643 | A | * | 10/1986 | Bai .................................. 604/43 |
| 4,955,856 | A | * | 9/1990 | Phillips ........................... 600/16 |
| 5,167,623 | A | * | 12/1992 | Cianci et al. .................... 604/43 |
| 5,190,528 | A | | 3/1993 | Fonger et al. |
| 5,275,580 | A | * | 1/1994 | Yamazaki ........................ 600/16 |
| 5,346,471 | A | * | 9/1994 | Raulerson ........................ 604/43 |
| 5,397,302 | A | * | 3/1995 | Weaver et al. ............ 604/93.01 |
| 5,464,398 | A | * | 11/1995 | Haindl ........................... 604/523 |
| 5,776,190 | A | * | 7/1998 | Jarvik ............................. 600/16 |
| 5,785,686 | A | | 7/1998 | Runge |
| 5,807,318 | A | * | 9/1998 | St. Goar et al. ............... 604/508 |
| 5,810,789 | A | | 9/1998 | Powers et al. |
| 5,827,220 | A | * | 10/1998 | Runge ........................... 604/509 |
| 5,858,009 | A | * | 1/1999 | Jonkman ........................ 604/264 |

(Continued)

FOREIGN PATENT DOCUMENTS

| EP | 1687055 B1 | 10/2008 |
| JP | H03-131265 | 6/1991 |

(Continued)

OTHER PUBLICATIONS

Anderson et al., Venovenous Extracorporeal Lite Support in Neonates Using a Double Lumen Catheter, ASAIO Transactions, 35(3):650-653, dated Jul.-Sep. 1989, 1 page.

(Continued)

*Primary Examiner* — Carl H Layno
*Assistant Examiner* — Eugene Wu
(74) *Attorney, Agent, or Firm* — Knobbe, Martens, Olson & Bear LLP

(57) ABSTRACT

This document relates to methods and materials for providing blood flow for a blood pump recipient. For example, cannulae that can be connected to the circulatory system of a mammal and can be used in conjunction with a blood pump (e.g., an assist device) are provided.

21 Claims, 5 Drawing Sheets

(56) References Cited

U.S. PATENT DOCUMENTS

| | | | |
|---|---|---|---|
| 5,868,703 A | | 2/1999 | Bertolero et al. |
| 5,868,717 A | * | 2/1999 | Prosl .............................. 604/264 |
| 5,916,193 A | * | 6/1999 | Stevens et al. ................. 604/509 |
| 6,059,760 A | | 5/2000 | Sandmore et al. |
| 6,123,725 A | | 9/2000 | Aboul-Hosn |
| 6,190,357 B1 | * | 2/2001 | Ferrari et al. ............ 604/102.01 |
| 6,206,849 B1 | | 3/2001 | Martin et al. |
| 6,482,171 B1 | | 11/2002 | Corvi et al. |
| 6,969,379 B1 | | 11/2005 | Aboul-Hosn et al. |
| 6,974,436 B1 | * | 12/2005 | Aboul-Hosn et al. ............. 604/9 |
| 7,347,810 B2 | | 3/2008 | Stamos |
| 2002/0188167 A1 | | 12/2002 | Viole et al. |
| 2003/0191425 A1 | * | 10/2003 | Rosenblatt et al. .......... 604/4.01 |
| 2005/0085761 A1 | * | 4/2005 | Wang et al. .................. 604/6.11 |
| 2005/0277804 A1 | | 12/2005 | Pecor |
| 2005/0277870 A1 | * | 12/2005 | Pecor .............................. 604/43 |
| 2007/0112334 A1 | | 5/2007 | Porter et al. |
| 2007/0149949 A1 | | 6/2007 | Porter et al. |
| 2009/0069786 A1 | | 3/2009 | Vesely et al. |
| 2009/0105545 A1 | | 4/2009 | Janis et al. |
| 2009/0171295 A1 | | 7/2009 | Porter et al. |

FOREIGN PATENT DOCUMENTS

| | | |
|---|---|---|
| JP | 2005-521525 | 7/2005 |
| WO | WO0012148 A2 | 3/2000 |
| WO | WO03068303 A2 | 8/2003 |

OTHER PUBLICATIONS

Yamazaki et al., A Miniature Intraventricular Axial Flow Blood Pump that is Introduced Through the Left Ventricular Apex, ASAIO Journal, 38: M679-M683, 1992, 5 pages.

Yamazaki et al., Long Term Animal Experiments With an Intraventricular Axial Flow Blood Pump, ASAIO Journal, 1997, 43: M696-M700, 5 pages.

Kolff et al., Minimally Invasive Left Ventricular Assist Device (miLVAD), ASAIO Journal, vol. 48(2), Mar.-Apr. 2002, p. 166, 1 page.

Reichenbach et al., A Single-Entry Percutaneous Cannula for RVAD Support, ASAIO 2003, 6 pages.

Avalon Laboratories receives FDA and European clearances to market 3 catheter devices, dated Jan. 15, 2009, 2 pages.

Dermaport™ device, 3 photos, device available prior to May 20, 2009, 3 pages.

Cezo et al., Novel Transaortic Double Barrel Ventricular Cannula, J. Med. Devices 3, Jun. 2009, vol. 3, Issue 2, 1 page.

International Search Report & Written Opinion for Application No. PCT/US2010/035424, dated Nov. 30, 2010, 15 pages.

U.S. Non-Final Office Action for U.S. Appl. No. 12/469,328, filed Apr. 25, 2011, 15 pages.

U.S. Final Office Action for U.S. Appl. No. 12/469,328, filed Oct. 14, 2011, 11 pages.

Reichenbach et al., A Single-Entry Percutaneous Cannula for Rvad Support, ASAIO Journal, vol. 49(2), Mar.-Apr. 2003, p. 175, 1 page.

U.S. Notice of Allowance for U.S. Appl. No. 12/469,328 dated Apr. 4, 2012, 16 pages.

Australian Examination Report for Application No. 2010249562 dated Jul. 19, 2012, 3 pages.

Canadian Office Action for Application No. 2,762,569 dated Jan. 21, 2013, 3 pages.

JP Office action in Japanese Application No. 2012-511994, dated May 21, 2013, 3 pages.

* cited by examiner

MULTI-LUMEN CANNULA

CROSS-REFERENCE TO RELATED APPLICATION

This application is a continuation (and claims the benefit of priority under 35 USC 120) of U.S. application Ser. No. 12/469,328, filed May 20, 2009, now allowed as U.S. Pat. No. 8,231,519, and titled "Multi-lumen Cannula." The disclosure of the prior application is considered part of (and is incorporated by reference in) the disclosure of this application.

BACKGROUND

1. Technical Field

This document relates to methods and materials for providing blood flow for a blood pump recipient. For example, this document provides cannulae that can be connected to the circulatory system of a mammal and can be used in conjunction with a blood pump (e.g., an assist device).

2. Background Information

Mechanical circulatory support (MCS) is a way of improving blood flow in a failing heart using an electrically or pneumatically powered blood pump. A ventricular assist device (VAD) is an implantable blood pump that works in conjunction with the recipient's own heart to pump sufficient blood throughout the body. Heart failure may affect the right side of the heart, limiting the ability of the heart to pump blood to the lungs, or the left side of the heart, resulting in an inability to pump sufficient oxygen-rich blood to the rest of the body. Often, both sides of the heart are affected, A VAD can provide short-term MCS while a recipient is awaiting cardiac transplant, or permanent MCS for a recipient who is not a candidate for transplantation, by delivering consistent blood flow to vital organs.

SUMMARY

This document relates to methods and materials for providing blood flow for a blood pump recipient. For example, this document provides cannulae that can be connected to the circulatory system of a mammal and can be used in conjunction with a blood pump (e.g., an assist device). In some cases, a cannula provided herein can have an eccentric multi-lumen design that can require a single insertion site. For example, a cannula, featuring a circular-shaped lumen nested in the notch of a reniform-shaped lumen and a thin, flexible septum, is provided. Cannulae provided herein can provide a blood-flow path with beneficial fluid dynamics and can reduce the complexity associated with blood pump placement.

In general, a cannula for use with a blood pump is described. The cannula includes a housing having a proximal region, a distal region, and an intermediate region located between the proximal and distal regions. The housing defines a first lumen and a second lumen. The first lumen includes (a) a proximal end located within the proximal region of the housing and adapted to engage the blood pump and (b) a distal end located within the distal region of the housing and adapted to be positioned within a cardiovascular system. The second lumen comprises (a) a proximal end located within the proximal region of the housing and adapted to engage the blood pump and (b) a distal end located within the intermediate region of the housing and adapted to be positioned within the cardiovascular system. One of the first and second lumens has a generally reniform cross-sectional shape in the intermediate region.

In another aspect, this document describes a method for implanting a cannula as described above into the heart of a mammal. The method comprises, or consists essentially of, puncturing the heart or a blood vessel of the mammal, and inserting a cannula into the chamber of the heart, so that the distal region of the cannula is positioned within a blood vessel of the mammal and the intermediate region of the cannula is positioned within a chamber of the heart of the mammal. The method can include connecting a blood pump to the proximal region of the cannula. The blood pump can receive blood from the heart through the second lumen of the cannula and pump blood to the blood vessel through the first lumen of the cannula. The distal end of the first lumen can be positioned in the aorta and the distal end of the second lumen can be positioned in the left ventricle. In another aspect, the distal end of the first lumen can be positioned in the pulmonary artery and the distal end of the second lumen can be positioned in the right ventricle.

In another aspect, this document describes a system for providing blood flow to a mammal. The system comprises, or consists essentially of, a cannula as described above and a blood pump. The proximal end of the first lumen of the cannula can be connected to the inflow of the blood pump and the proximal end of the second lumen of the cannula can be connected to the outflow of the blood pump.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

This document relates to methods and materials for providing blood flow for a blood pump recipient. For example, this document provides cannulae that can be connected to the circulatory system of a mammal and can be used in conjunction with a blood pump (e.g., an assist device). In some cases, a cannula provided herein can have an eccentric multi-lumen design that can require a single insertion site, For example, a cannula can feature a circular-shaped lumen nested in the notch of a reniform-shaped lumen and can feature a thin, flexible septum.

Figure 1:
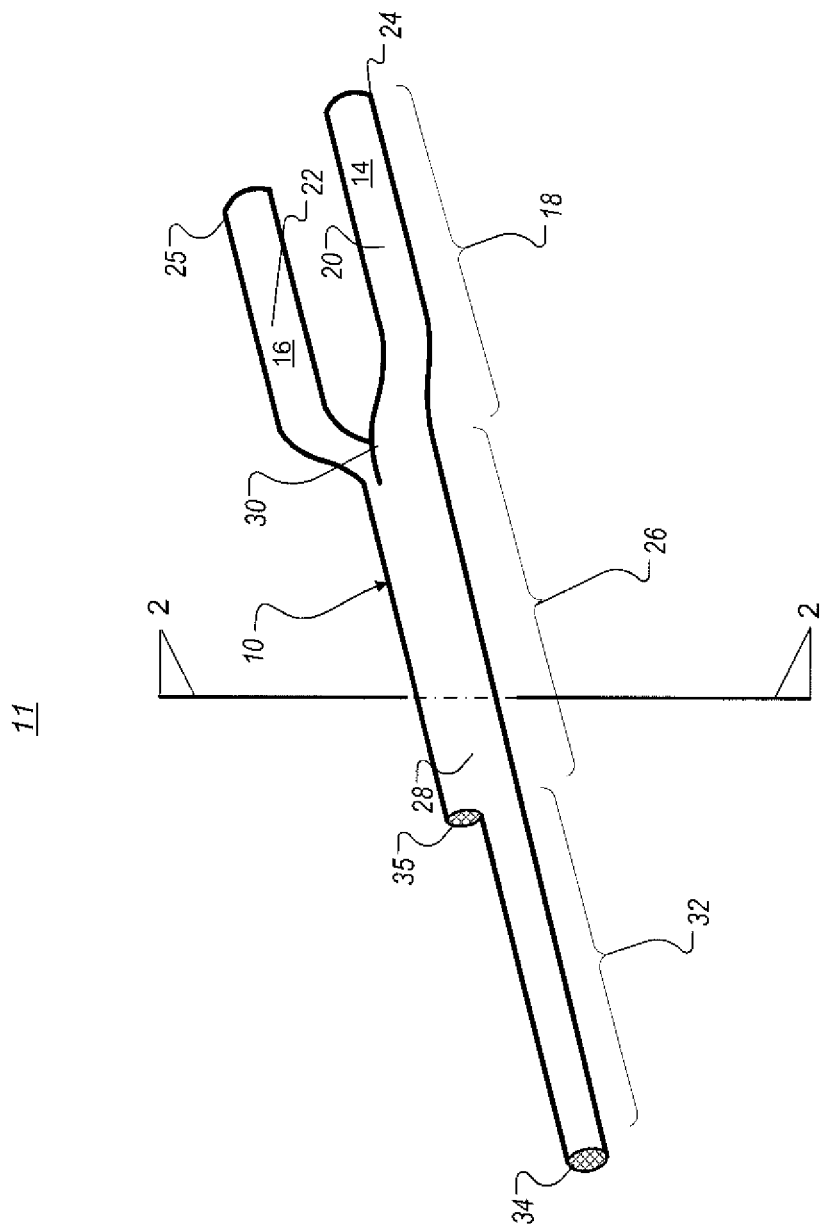
FIG. 1 is a perspective view of the housing of one exemplary embodiment of a cannula.

In reference to FIG. 1, cannula 11 for use with a blood pump can be constructed from single housing 10 having proximal region 18, distal region 32, and intermediate region 26 located between region 18 and region 32. Housing 10 can define first lumen 14 and second lumen 16. First lumen 14 can have proximal end 24 located within proximal region 18 of housing 10 and distal end 34 located within distal region 32 of housing 10. Second lumen 16 can have proximal end 25 located within proximal region 18 and distal end 35 located within intermediate region 26.

Proximal ends 24 and 25 can be adapted to engage a blood pump releasably. As used herein, "adapted to releasably engage a blood pump" refers to any feature that allows interchangeability of a blood pump without the need to remove cannula 11 from the circulatory system. For example, proximal ends 24 and 25 can be constructed to permit connection to a blood pump via additional tubing, rigid fittings, or connectors. In some cases, proximal ends 24 and 25 can include additional tubing of any length or diameter suitable for being connected to a blood pump. In some cases, additional tubing can have multiple segments, which may be areas in which additional tubing is compressed and folded back on itself, to permit for articulation of additional tubing. For example, the construction of the tubing may be similar to the construction of a flexible drinking straw, but providing an inner surface that is more rounded than that of a drinking straw. In other examples, the tubing may be constructed so that the tubing segments are similar to crimps in a vascular graph, convolutions in a pair of bellows, or fluting within corrugated cardboard. In some cases, additional tubing may be flared at both ends to engage proximal end 24 or 25 at one end and a blood pump at another end. In some cases, additional tubing may be bonded or compressed onto a separate rigid fitting for connection to a blood pump.

In some cases, releasable engagement of proximal ends 24 and 25 can be accomplished with connectors of an appropriate form that allow for reliable connections. For example, appropriate connectors can be screw rings that can be tightened to form a fluid-tight seal so as to prevent fluids from leaking out of the system during operation. (See e.g., U.S. Pat. Pub. No. 2006/0074271). Other suitable connectors can include twist-and-lock connectors, connectors with bolted flanges, circumferential clamps, compressive fitting, snap fit, or simple threaded connections. Suitable connectors can be provided with appropriate locking features that prevent them from loosening after a blood pump has been implanted. Various connectors can be sized to allow interchangeability of a blood pump without the need to remove the cannula from the circulatory system. In some cases, proximal ends 24 and 25 can be adapted to engage a blood pump by different engagement means. For example, if proximal end 24 is adapted to engage the outflow port of a blood pump, proximal end 25 can be adapted to engage the inflow port of the blood pump.

Additionally, in some implementations, the cannula or cannula structure may be permanently attached to the pump. For example, the inflow or outflow portions of the cannula could be integrated into the pump housing.

Distal ends 34 and 35 can be adapted to be positioned within a cardiovascular system. In some cases, distal ends 34 and 35 can bifurcate or branch from the intermediate region of the cannula. As used herein, "adapted to be positioned within a cardiovascular system" refers to any feature that permits cannula 11 to be inserted into a heart or vasculature of a blood pump recipient and provides for appropriate blood flow through lumens 14 and 16. In some cases, distal ends 34 and 35 can have a single opening in line with lumens 14 and 16. In some cases, distal ends 34 and 35 can have a lip adapted to use lumens 14 and 16 as inflow or outflow lumens. For example, a lip of distal ends 34 and 35 can be blunt, tapered, or spoon shaped.

In some cases, a feature that permits placement of distal end 34 in the cardiovascular system can be different from a feature that permits placement of distal end 35 in the cardiovascular system. For example, distal end 34 can be flexible to permit manipulation within the cardiovascular tissue, whereas distal end 35 can be rigid. In some cases, distal end 35 can be adapted for use as an inflow lumen and distal end 34 can be adapted for use as an outflow lumen. In some cases, distal end 34 can have an opening along distal region 32 transverse to lumen 14. A suitable opening can be several slits to permit blood flow, for example.

In some cases, distal end 34 can include a sensor. A suitable sensor can include pressure sensors or thermisters, for example. There are many different cannula tip geometries that are well known to a person of ordinary skill in the art. Any one of these tip geometries may be used. Any description within this document of a particular tip geometry is not intended to be limiting, but is given merely for illustrative purposes, In further reference to FIG. 1, regions 18, 32, and 26 of housing 10 can have any suitable size or shape for use with a blood pump. For example, the length of any of regions 18, 32, and 26 can depend on an application of cannula 11. Suitable applications for cannula 11 can be providing blood flow for a blood pump recipient of any age and size, at any length required to connect a recipient's heart and a blood pump. For example, cannula 11 can be implanted in an average adult. In some cases, distal region 32 can be between about 3 cm and about 12 cm in length for use in an average adult. For example, intermediate region 26 can be between about 5 cm and about 20 cm (or even up to about 50 cm if, for example, the cannula is femorally inserted) in length when cannula 11 is used with a blood pump implanted in the abdominal cavity of an average adult. For example, cannula 11 can be implanted in the body of a child. In some cases, the length of proximal region 18 can be less than about 5 cm when cannula 11 is implanted in the body of a child. In some cases, the length of intermediate region 26 can be less than about 5 cm, when cannula 11 is implanted in a child. In some cases, the length of distal region 32 can be less than about 3 cm, if cannula 11 is implanted in a child.

Suitable applications for cannula 11 can be providing blood flow in conjunction with any blood pump. For example, cannula 11 can be used with an external blood pump or an implanted blood pump. In some cases, proximal region 18 can be greater than 20 cm in length when cannula 11 is attached to an external blood pump. In some cases, proximal region 18 can be between about 5 cm and about 20 cm in length, when cannula 11 is used with an implanted VAD. For example, intermediate region 26 can be longer than 20 cm for use with a blood pump implanted in a leg of a recipient.

Suitable applications for cannula 11 can require surgical or percutaneous placement of cannula 11. For example, distal region 32 can be surgically inserted through the lowest superficial part of a heart (apex) and extended across the aortic valve or placed from a peripheral artery, by crossing the aortic valve in a retrograde fashion. In some cases, the length of distal region 32 can depend on the approach the surgeon uses to connect cannula 11 to the cardiovascular system. For example, for certain surgical placements, distal region 32 can be greater than 12 cm in length.

In some cases, housing 10 can have a single outer wall 28 that houses lumens 14 and 16 in the intermediate region 26 and proximal region 18 and lumen 14 in distal region 32. The diameter of outer wall 28 can depend on the blood flow requirements of a particular recipient. For example, the diameter of outer wall 28 can be less than about 5 mm if cannula 11 is implanted in a child. When cannula 11 is placed in an average adult, for example recipient, the diameter of outer wall 28 can be between about 5 mm and about 22 mm. If cannula 11 is placed in a large adult recipient, for example, the diameter of outer wall 28 can be greater than 22 mm.

In some cases, housing 10 can have outer walls associated with three areas of the housing. For example, a bifurcated housing has three areas (e.g., a first branch area, a second branch area, and a third area on the housing before the bifurcation). The first branch area has a first outer wall 20, the second branch area has a second outer wall 22, and the third area of the housing has an outer wall 28. Outer wall 28 can encompass intermediate region 26 and distal region 32. In some cases, first outer wall 20 can house lumen 14 in proximal region 18, and second outer wall 22 can house lumen 16 in proximal region 18. In some cases, housing 10 can have fork 30. For example, fork 30 can provide a transition from intermediate region 26 and proximal region 18 by dividing outer wall 28 into outer walls 20 and 22.

Single outer wall 28 can have any suitable size or shape for use in cannula 11. For example, outer wall 28 can be generally cylindrical (e.g., including cylinders having the cross-sectional shape of an oval, a circle, or a convex polygon, such as an octagon, a nonagon or a decagon). In some cases, the shape of outer wall 28 can contribute to the flexibility of cannula 11. For example, outer wall 28 can be rigid or flexible. In some cases, outer wall 28 that houses proximal region 18 can be adapted to engage a blood pump. For example, outer wall 28 can be bonded or compressed onto a separate rigid fitting that has a lip that can be held by connectors of a blood pump. In some cases, outer wall 28 can be furcated to allow distal end 35 to be positioned independently of lumen 14 in intermediate region 26.

Outer walls 20 and 22 can have any appropriate size and shape. For example, the length of outer walls 20 and 22 can be the same as the length of proximal region 18. If inflow and outflow ports on a blood pump are sufficiently close, outer walls 20 and 22 can be less than about 5 cm in length, for example. In some cases, outer walls 20 and 22 can have multiple segments, which may be areas in which proximal region 18 is compressed and folded back on itself, to permit for articulation of proximal region 18. In some cases, outer wall 20 or 22 can be flared at one end. In some cases, outer walls 20 and 22 can be adapted for engaging a blood pump as discussed for outer wall 28.

Any appropriate material for the manufacture of cannula 11 can be used to construct outer walls 28, 20, and 22. Examples include, without limitation, silicone rubbers, ethylene vinyl acetate, polyurethanes, polyether polyester copolymers, polyvinyl chloride, polyether block amide, and polypropylene oxide. In some cases, outer walls 28, 20, and 22 can be formed in whole or in part from one material or a combination of materials. In some cases, outer walls 28, 20, and 22 can be manufactured from different materials.

In some cases, the surfaces of housing 10 can be treated to optimize performance of cannula 11 in the body of a blood pump recipient. For example, surfaces of housing 10 can be textured or coated. In some cases, outer walls 28, 20 and 22 and the surface of the lumens 14 and 16 can be treated with a layer of textured silicone. In some cases, outer walls 28, 20, and 22 can be roughened by abrasion. In some cases, outer walls 28, 20 and 22 and the surface of the lumens 14 and 16 of can be coated with an antithrombotic (e.g., heparin or heparan sulfate), an anti-coagulant (e.g., bishydroxy-coumarin or warfarin) or an anti-platelet (e.g., ticlopidine or clopidogrel) agent. In some cases, the surfaces of housing 10 can have a combination of textured and coated surfaces. For example, housing 10 can feature textured surfaces on outer walls 28, 20, and 22, and coated surfaces in lumens 14 and 16.

Figure 2:
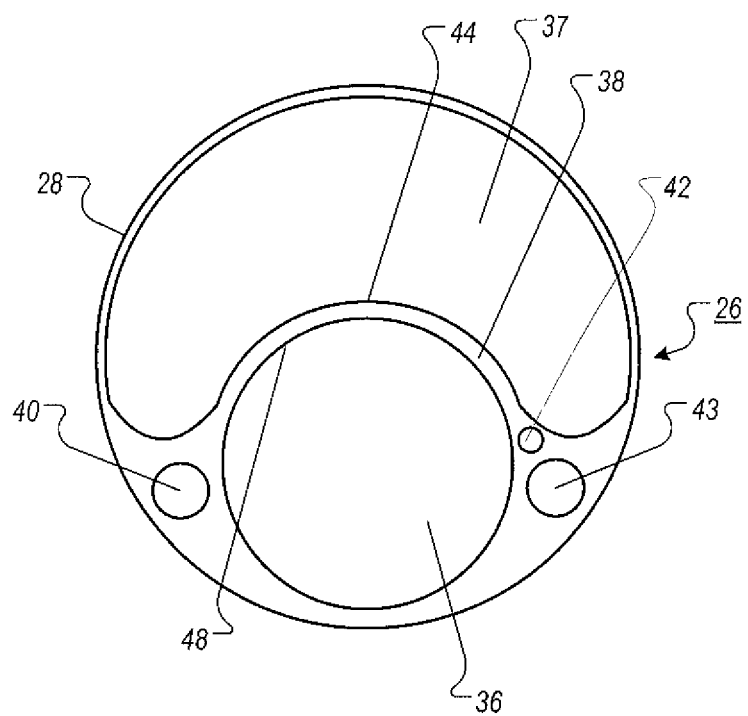
FIG. 2 is a cross-sectional view of the intermediate region of the housing as depicted in FIG. 1.

Referring to FIG. 2, a cross-section of intermediate region 26 can define lumens 36 and 37. Lumens 36 and 37 can represent a cross-section of lumens 14 and 16. For example, if the cross-sectional shape of lumen 14 is generally circular, then the cross-sectional shape of lumen 16 can be generally reniform. In some cases, if the cross-sectional shape of lumen 14 has a generally reniform shape, then the cross-sectional of lumen 16 can have a generally circular shape.

Lumens 36 and 37 can have any appropriate size and shape for providing a path for blood flow. In some cases, lumen 36 can have a generally circular cross-sectional shape (e.g., a circle, an oval or a convex polygon, such as a decagon, a dodecagon and a tetradecagon). In some cases, lumen 37 can have a generally reniform, or kidney-like, cross-sectional shape. For example, lumen 37 can feature a notch and can be circular or roughly circular. In some cases, the cross-sectional shape of lumen 37 can be bilaterally symmetrical. For example, there can be a longitudinal plane over which the reflection image of a half of lumen 37 is another half of lumen 37.

Figure 4:
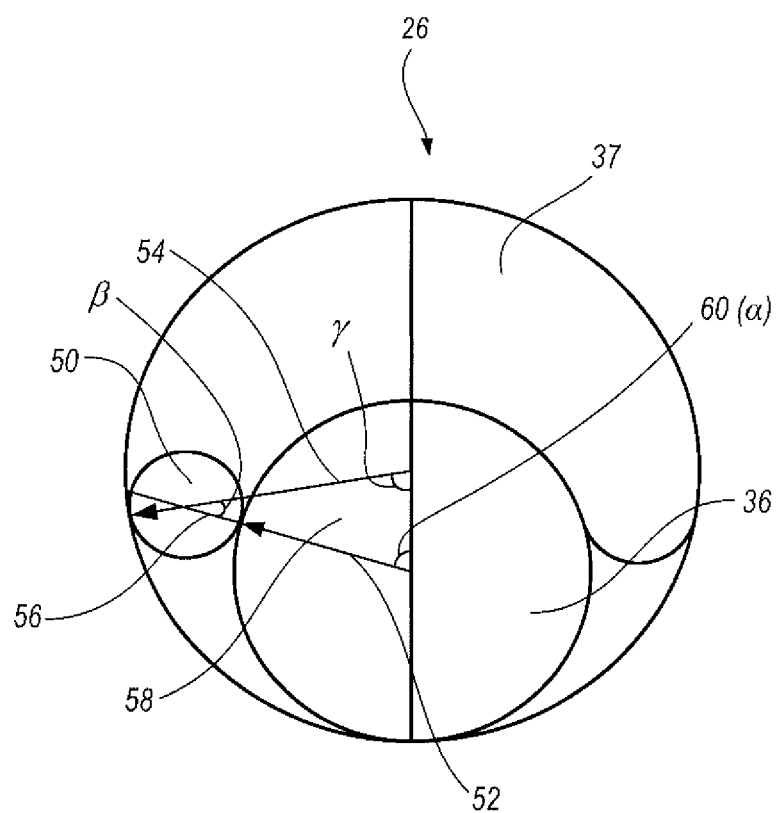
FIG. 4 is a schematic depicting geometric relationships of lumens.

The size and shape of lumen 37 can be any size and shape that permits blood flow. In some cases, lumen 37 can have rounded corners. For example, the radius of the rounded corners can be greater than about ten percent of the radius of the largest circle that can be inscribed within lumen 37. In some cases, the width of lumen 37 can depend on the diameter of the cross-section of intermediate region 26. For example, the diameter of the largest circle that can be inscribed in lumen 37 and the minimum diameter of intermediate region 26 can relate to each other by a ratio between about 0.2 and about 0.6. In another example, the diameter of the largest circle that can be inscribed in lumen 37 and the minimum inside diameter of lumen 36 can relate to each other by a ratio between about 0.25 and about 1.5. The geometric relationships that give rise to these dimensions are depicted in FIG. 4 and are described in detail below.

A cross-sectional view of intermediate region 26 can include septum 38 located between lumens 36 and 37. In some cases, septum 38 is configured to form convex surface 44 of lumen 37 and concave surface 48 of lumen 36. In some cases, septum 38 can be configured to support the pressure produced across septum 38 through wall tension. In some cases, septum 38 can be made very thin. For example, the septum 38 can be between about 0.1 mm and about 2.0 mm thick. In some cases, septum 38 can be flexible. For example, the shape of septum 38 can demonstrate directional flexibility as compared to a flat septum. For example, septum 38 can permit cannula 11 to bend in the plane of septum 38. In some implementations, the septum 38 may be defined to include any material between the two lumens.

Intermediate region 26 can have a malleable wire 42. In some cases, malleable wire 42 can be threaded into intermediate region 26. For example, malleable wire 42 can be located adjacent to lumens 14 and 16. In some cases, malleable wire 42 can extend along distal region 32 to permit a surgeon to manipulate distal end 34 through a heart and into the vasculature of a blood pump recipient.

Any suitable material can be used to construct malleable wire 42 including, medical grade stainless steel, such as an SS 303 or SS 304 stainless steel, for example. Other malleable materials besides stainless steel also may be used in the construction of the wire. In some cases, malleable wire 42 can have a diameter that permits the wire to be easily shaped by hand into a desired configuration yet hold its shape while housing 10 is manipulated in the recipient during placement. For example, malleable wire 42 can have stiffness about $28 \times 10^6$ psi as defined by ASTM D747 Standard Test Method. In some cases, the appropriate diameter of malleable wire 42 can depend on the size of housing 10 and wire material. In some cases, the diameter of malleable wire 42 can be from about 0.36 mm (0.014 in) to about 1.6 mm (0.063 in). In some implementations, the malleable wire 42 need not have any particular cross-section. For example, the wire 42 may be formed as a coil.

In further reference to FIG. 2, intermediate region 26 can define a third lumen 40 and a fourth lumen 43. In some cases, lumens 40 and 43 can be located between lumen 36 and the outer wall 28, below the area defined by the rounded corners of lumen 37. For example, lumen 40 can be located on one side of lumen 36, and lumen 43 can be located on the opposite side of lumen 36. In some cases, lumens 40 and 43 can have generally circular cross-sectional shapes, including ovals, circles, and polygons. In some cases, the cross-sectional shape of lumen 40 can differ from the cross-sectional shape of lumen 43. In some cases, the centers of lumens 40 and 43 can lie on the axis that transects lumen 36 along its diameter and is perpendicular to a bilateral axis of the lumen 37.

Lumens 40 and 43 can perform any appropriate function in cannula 11. In some cases, lumens 40 and 43 can be used to minimize structural rigidity. For example, lumens 40 and 43 can be hollow to reduce the rigidity of intermediate region 26. In some cases, lumen 40 can be used to provide local access to the circulatory system. For example, lumen 40 can include a fluid port. A fluid port placed in intermediate region 26 can provide local access to the circulatory system for purposes of pressure measurement, blood sampling, or fluid administration. In some cases, the intermediate region or lumen 40 can have a fluid port that is adapted to deliver fluid into the circulatory system or enable a user to withdraw blood from a blood pump recipient.

In certain cases, the intermediate region and/or lumen 40 can be utilized to introduce a sensor into the circulatory system. For example, lumen 40 can be located in intermediate region 26 specifically to house a probe or sensor. An appropriate location for a sensor can be determined by probe or sensor type. For example, suitable probes or sensors can be mechanical, piezoelectric, fiber optic, ultrasonic, or micro-electro-mechanical probes or sensors. In some cases, a probe or sensor can be a single probe or sensor or a combination of probes or sensors. In some cases, a probe or sensor can be used to provide real-time information about blood flow or temperature. For example, a probe or sensor can be a pressure transducer, a flow sensor, or a thermister. In certain cases, the intermediate region can be adapted for routing a sensor or sensor lead, sensor wire, or an electrode attached to a sensor.

Figure 3:
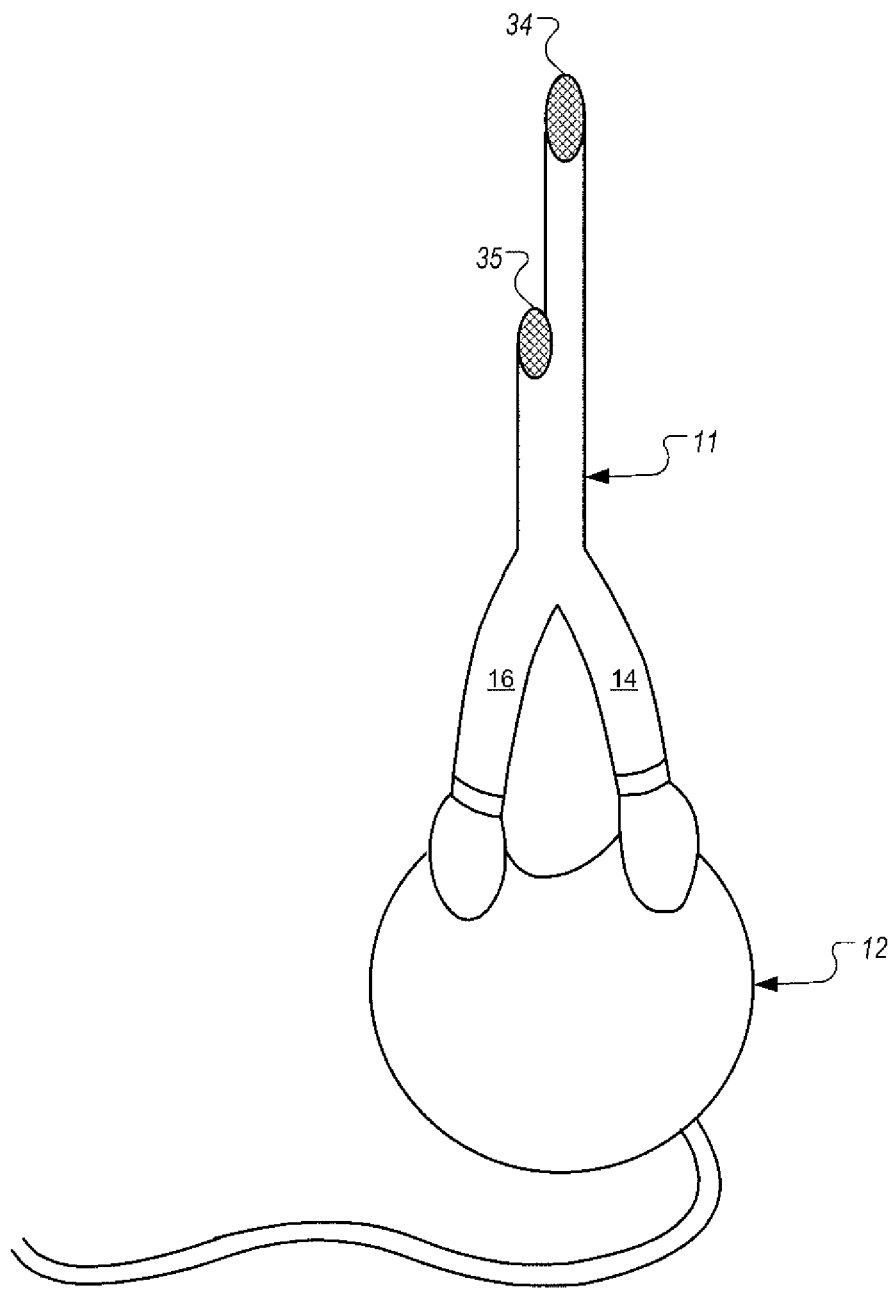
FIG. 3 is front view of a cannula connected to a blood pump.

In some implementations, the sensor is not in the fluid port as direct blood contact is not necessary for certain sensors. In such cases, the lumen 40 may house the sensor and wires. Referring to FIG. 3, subsequently described, the location of a sensor could be anywhere along cannula 11. For example, a sensor could be placed at a position associated with distal end 35. The position of the sensor may depend on the type of sensor and what is being measured.

FIG. 3 depicts an exemplary embodiment of a cannula 11 for use with a blood pump 12. Blood pump 12 can be one of any number of blood pumps available for providing mechanical circulatory support. For example, a blood pump can be implanted or implantable in a blood pump recipient. In some cases, a blood pump can be an external pump, such as a cardiopulmonary bypass pump. A blood pump can be a ventricular assist device (VAD). For example, depending on the placement of the cannula, a blood pump can be a left ventricular assist device (LVAD) or a right ventricular assist device (RVAD). Additionally, the blood pump can serve as a bilateral ventricular assist device (BiVAD). In some cases, a blood pump can be a continuous-flow blood pump or a pulsatile-flow blood pump.

Referring to FIG. 4, the size of lumen 36, and the shape and size of lumen 37 can determine the flow characteristics associated with cannula 11. In some cases, the shape of lumen 37 can be limited by the size of intermediate region 26 and lumen 36.

As depicted in FIG. 4, lumen 36 has radius ($R_1$) 52, a cross-section of intermediate region 26 has radius ($R_2$) 54, and circle 50 inscribed in a rounded corner of lumen 37 has radius ($R_3$) 56. Triangle 58 (t), with vertices at the centers of lumen 36, intermediate region 26 and circle 50, has angles α 60, β, and γ, and sides a, b, and c. The area ($A_t$) of triangle 58 can be described using basic trigonometry relations:

(Law of cosines)
$$c^2 = a^2 + b^2 - 2 \cdot a \cdot b \cdot \cos(\gamma)$$

(Law of sines)
$$\frac{a}{\sin(\alpha)} = \frac{b}{\sin(\beta)} = \frac{c}{\sin(\gamma)}$$

So:
$$\gamma = \operatorname{acos}\left(\frac{a^2 + b^2 - c^2}{2a \cdot b}\right)$$

$$\beta = \operatorname{asin}\left(\frac{b}{c} \cdot \sin(\gamma)\right)$$

$$\alpha = \operatorname{asin}\left(\frac{a}{c} \cdot \sin(\gamma)\right) = \pi - \beta - \gamma$$

$$A_t = \frac{1}{2} \cdot a \cdot c \cdot \sin(\beta) = \frac{1}{2} \cdot a \cdot b \cdot \sin(\gamma) = \frac{1}{2} \cdot b \cdot c \cdot \sin(\alpha)$$

Relating the triangle sides to the cannula:

$$a = R_2 - R_3$$

$$b = R_2 - R_1$$

$$c = R_1 + R_3$$

$$\gamma = \operatorname{acos}\left[\frac{(R_2 - R_3)^2 + (R_2 - R_1)^2 - (R_1 + R_3)^2}{2(R_2 - R_3) \cdot (R_2 - R_1)}\right]$$

$$\beta = \operatorname{asin}\left(\frac{R_2 - R_1}{R_1 + R_3} \cdot \sin(\gamma)\right)$$

$$\alpha = 180 - \gamma - \beta$$

The area defined by the equation:

$$A_t \frac{1}{2}(R_2 - R_3)(R_1 + R_3)\sin(\beta)$$

Further simplifying (not carrying the extra angle):

$$\beta = \operatorname{asin}\left[\frac{R_2 - R_1}{R_1 + R_3} \cdot \sin\left[\operatorname{acos}\left[\frac{(R_2 - R_3)^2 + (R_2 - R_1)^2 - (R_1 + R_3)^2}{2(R_2 - R_3) \cdot (R_2 - R_1)}\right]\right]\right]$$

The perimeter ($S_o$) of lumen 37 can be determined by:

$$S_o = 2 \cdot [(\pi - \gamma) \cdot R_2 + (\pi - \beta) \cdot R_3 + \alpha \cdot R_1]$$

The area of lumen 37 ($A_o$) is given by:

$$A_o = (\pi \cdot R_2^2 - \pi \cdot R_1^2) \ldots +$$
$$-2 \cdot \left(\frac{\gamma}{2 \cdot \pi} \cdot \pi \cdot R_2^2 - \frac{\pi - \alpha}{2 \cdot \pi} \cdot \pi \cdot R_1^2 - A_t - \frac{\pi - \beta}{2 \cdot \pi} \cdot \pi \cdot R_3^2\right) =$$
$$(\pi - \gamma)R_2^2 - R_1^2 \alpha + (\pi - \beta)R_3^2 + 2A_t$$

The relation between radius 56 ($R_3$) and angle α60 can be found from the cosine law:

$$\cos\alpha = \frac{(R_1 + R_3)^2 + (R_2 - R_1)^2 - (R_2 - R_3)^2}{2(R_1 + R_3)(R_2 - R_1)}$$

Expanding gives:

$$2\cos\alpha = \frac{R_1^2 + R_3^2 + 2R_1 R_3 + R_2^2 + R_1^2 - 2R_1 R_2 - R_2^2 - R_3^2 + 2R_2 R_3}{R_1 R_2 - R_1^2 + R_3(R_2 - R_1)}$$

Simplifying and rearranging yields:

$$2(R_1 R_2 - R_1^2)\cos\alpha + 2R_3(R_2 - R_1)\cos\alpha = 2R_1^2 - 2R_1 R_2 + 2R_3(R_1 + R_2)$$
$$2(R_1 R_2 - R_1^2)\cos\alpha - 2R_1^2 + 2R_1 R_2 = 2R_3(R_1 + R_2 - (R_2 - R_1)\cos\alpha)$$
$$R_3 = \frac{R_1(R_2 - R_1)\cos\alpha + R_1(R_2 - R_1)}{R_1 + R_2 - (R_2 - R_1)\cos\alpha}$$
$$R_3 = \frac{R_1(R_2 - R_1)(1 + \cos\alpha)}{(R_1 + R_2) - (R_2 - R_1)\cos\alpha}$$

With $R_2=1$, values for radius 56 at angle α60 from 40° to 140° and radius $R_1$ are listed in table 1 below.

Assuming incompressible and fully developed steady flow in a straight tube, the Navier Stoke's equation can be simplified to Poisson's equation.

$$0 = -\frac{\partial P}{\partial z} + \mu\left(\frac{\partial^2 w}{\partial x^2} + \frac{\partial^2 w}{\partial y^2}\right)$$

Let $$X = x/R_2$$
$$Y = y/R_2$$
$$W = w/V_{ref}$$

Where $R_2$ 54 is the radius of intermediate region 26 and $V_{ref}$ is the mean flow velocity in circular pipe of radius $R_2$.

Use Poiseulle flow as reference, we have:

$$Q_{ref} = \frac{\pi R_2^4}{8\mu}\left(-\frac{\partial P}{\partial z}\right)$$
$$V_{ref} = \frac{Q_{ref}}{\pi R_2^2} = \frac{R_2^2}{8\mu}\left(-\frac{\partial P}{\partial z}\right)$$

Substitute into the Poisson equation gives the non-dimensional form, $$-8 = \left(\frac{\partial^2 W}{\partial X^2} + \frac{\partial^2 W}{\partial Y^2}\right) \qquad (1)$$

For wall shear rate, we have:

$$\tau = \mu \frac{dw}{dn}$$

TABLE 1

| | Angle α (degree) | | | | | | | | | | |
|---|---|---|---|---|---|---|---|---|---|---|---|
| $R_1$ | 40 | 50 | 60 | 70 | 80 | 90 | 100 | 110 | 120 | 130 | 140 |
| (degree/radian) | 0.6981 | 0.8727 | 1.0472 | 1.2217 | 1.3963 | 1.5708 | 1.7453 | 1.9199 | 2.0944 | 2.2689 | 2.4435 |
| 0.250 | 0.4902 | 0.4011 | 0.3214 | 0.2533 | 0.1965 | 0.1500 | 0.1123 | 0.0819 | 0.0577 | 0.0387 | 0.0240 |
| 0.275 | 0.4893 | 0.4049 | 0.3277 | 0.2605 | 0.2036 | 0.1564 | 0.1176 | 0.0861 | 0.0609 | 0.0409 | 0.0255 |
| 0.300 | 0.4856 | 0.4058 | 0.3316 | 0.2657 | 0.2091 | 0.1615 | 0.1221 | 0.0898 | 0.0636 | 0.0429 | 0.0268 |
| 0.325 | 0.4795 | 0.4044 | 0.3332 | 0.2691 | 0.2132 | 0.1656 | 0.1257 | 0.0928 | 0.0660 | 0.0446 | 0.0279 |
| 0.350 | 0.4715 | 0.4009 | 0.3329 | 0.2707 | 0.2158 | 0.1685 | 0.1285 | 0.0952 | 0.0679 | 0.0460 | 0.0288 |
| 0.375 | 0.4619 | 0.3956 | 0.3309 | 0.2709 | 0.2172 | 0.1705 | 0.1306 | 0.0971 | 0.0694 | 0.0471 | 0.0296 |
| 0.400 | 0.4507 | 0.3887 | 0.3273 | 0.2696 | 0.2174 | 0.1714 | 0.1319 | 0.0984 | 0.0706 | 0.0480 | 0.0302 |
| 0.425 | 0.4384 | 0.3804 | 0.3223 | 0.2670 | 0.2164 | 0.1715 | 0.1324 | 0.0991 | 0.0713 | 0.0486 | 0.0306 |
| 0.450 | 0.4249 | 0.3708 | 0.3160 | 0.2632 | 0.2144 | 0.1707 | 0.1323 | 0.0994 | 0.0717 | 0.0490 | 0.0309 |
| 0.475 | 0.4105 | 0.3601 | 0.3085 | 0.2584 | 0.2115 | 0.1691 | 0.1316 | 0.0992 | 0.0718 | 0.0492 | 0.0311 |
| 0.500 | 0.3953 | 0.3485 | 0.3000 | 0.2525 | 0.2076 | 0.1667 | 0.1302 | 0.0984 | 0.0714 | 0.0490 | 0.0311 |
| 0.525 | 0.3793 | 0.3359 | 0.2905 | 0.2456 | 0.2029 | 0.1635 | 0.1282 | 0.0972 | 0.0707 | 0.0487 | 0.0309 |
| 0.550 | 0.3627 | 0.3225 | 0.2802 | 0.2379 | 0.1973 | 0.1597 | 0.1256 | 0.0956 | 0.0697 | 0.0481 | 0.0306 |
| 0.575 | 0.3454 | 0.3084 | 0.2690 | 0.2294 | 0.1910 | 0.1552 | 0.1225 | 0.0935 | 0.0684 | 0.0472 | 0.0301 |
| 0.600 | 0.3277 | 0.2936 | 0.2571 | 0.2201 | 0.1840 | 0.1500 | 0.1188 | 0.0909 | 0.0667 | 0.0462 | 0.0294 |
| 0.625 | 0.3094 | 0.2782 | 0.2446 | 0.2102 | 0.1763 | 0.1442 | 0.1146 | 0.0880 | 0.0647 | 0.0449 | 0.0287 |
| 0.650 | 0.2907 | 0.2623 | 0.2314 | 0.1995 | 0.1680 | 0.1379 | 0.1099 | 0.0846 | 0.0623 | 0.0433 | 0.0277 |

Where n is the direction normal to the wall. In non-dimensional form, it is:

$$\frac{dw}{dn} = \frac{V_{ref}}{R_2}\left(\frac{dW}{dN}\right)$$

This simplifies to:

$$\frac{dw}{dn} = \frac{R_2}{8\mu}\left(-\frac{\partial P}{\partial z}\right)\left(\frac{dW}{dN}\right) \quad (2)$$

Solving (1) numerically with appropriate boundary equations we obtain the non-dimensionalized values of velocity W from which we can calculate the non-dimensional flow rate $Q^*$, wall shear rate $dW/dn$, area $A^*$. The dimensional values can be evaluated by the following conversion relations:

$$\frac{dw}{dn} = \frac{dW}{dn}\frac{R_2}{8\mu}\left(-\frac{\partial P}{\partial z}\right) \quad (3)$$

$$Q = Q^* R_2^2 V_{ref} = Q^*\frac{R_2^4}{8\mu}\left(-\frac{\partial P}{\partial z}\right) \quad (4)$$

$$A = A^* R_2^2 \quad (5)$$

$$w_{max} = W_{max} V_{ref} = W_{max}\frac{R_2^2}{8\mu}\left(-\frac{\partial P}{\partial z}\right) \quad (6)$$

The solution for the fluid dynamics of a conduit with cross-sections defined by lumens 36 and 37 can be converted to dimensional units as follows:

1 Poise=1 gm/cm-sec
1 cP=0.01 Poise=0.01 gm/cm-sec
1 Pa=1 N/m$^2$=1 kg-m/sec$^2$-m$^2$=10 gm/cm-sec$^2$
1 mmHg=0.1333223684211 kPa=1333.223684211 gm/cm-sec$^2$
1 litre/min=1000 cm$^3$/min=16.67 cm$^3$/sec Therefore, if the pressure gradient ($\partial P/\partial z$) is expressed in mmHg/cm, the shear rate ($\gamma$) in sec$^{-1}$, the viscosity ($\mu$) in cP, the velocity (w) in cm/sec, the flow rate (Q) in l/min, the dimensions x and y in cm, the diameter (D), the radius (r) in cm, and the area (A) in cm$^2$, Poisson's equation, can be expressed in dimensional form, as follows:

$$\left(\frac{\partial P}{\partial z}\right)\times 1333.2236842 \; gm/cm^2\text{-}sec^2 =$$
$$\mu\times 0.01 \; gm/cm\text{-}sec \times\left(\frac{\partial^2 w}{\partial x^2}+\frac{\partial^2 w}{\partial y^2}\right) cm/sec\text{-}cm^2$$

Giving $$\frac{1}{\mu}\left(\frac{\partial P}{\partial z}\right)\times 133322.36842 = \left(\frac{\partial^2 w}{\partial x^2}+\frac{\partial^2 w}{\partial y^2}\right)$$

For conversion from non-dimensional values to actual values:
Wall shear rate calculation, the factor $$\frac{R_2}{8\mu}\left(-\frac{\partial P}{\partial z}\right)$$

will be, $$\frac{R_2}{8\mu}\frac{cm}{0.01\; gm/cm\text{-}sec}\left(-\frac{\partial P}{\partial z}\right)\times 1333.22368 \frac{gm}{cm\text{-}sec^2}\frac{1}{cm} =$$
$$\frac{1333.22368}{8\times 0.01}\frac{R_2}{\mu}\left(-\frac{\partial P}{\partial z}\right)$$

OR $$\frac{dw}{dn} = \frac{dW}{dn}\times 16665.29605\frac{R_2}{\mu}\left(-\frac{\partial P}{\partial z}\right) sec^{-1}$$

Flow rate calculation will be, $$\frac{1}{16.67}\frac{1}{cm^3/sec}\frac{R_2^4}{8\mu}\frac{cm^4}{0.01\; gm/cm\text{-}sec}$$
$$\left(-\frac{\partial P}{\partial z}\right)\times 1333.22368\frac{gm}{cm\text{-}sec^2}\frac{1}{cm}$$

OR $$Q = Q^*\times 999.7178\times\frac{R_2^4}{\mu}\left(-\frac{\partial P}{\partial z}\right) l/min$$

Area calculation is dependent on actual value of radius ($R_2$) 54 of intermediate region 26, such that, $$A = A^* R_2^2 cm^2$$

Velocity calculation will have the same factor as shear rate.

$$w_{max} = W_{max}\times 16665.29605\frac{R_2^2}{\mu}\left(-\frac{\partial P}{\partial z}\right) cm/sec$$

For Poiseulle flow, $$Q = \frac{\pi D^4}{128\mu}\left(-\frac{\partial P}{\partial Z}\right)$$

Average flow velocity $V_{ave}$ is $$V_{ave} = \frac{Q}{A}$$

Maximum velocity $V_{max}$ is $V_{max}=2V_{ave}$
Shear rate $\gamma$ at radius r is $$\gamma = \frac{r}{2\mu}\left(-\frac{\partial P}{\partial z}\right)$$

Therefore, $$Q\times 16.67\; cm^3/sec =$$
$$\frac{\pi\times D^4 cm^4}{128\times\mu\times 0.001\; gm/cm\text{-}sec}\times 1333.22368\; gm/cm\text{-}sec^2 1\bigg/cm\left(-\frac{\partial P}{\partial z}\right)$$

Giving $$\frac{Q \times \mu}{196.3333937 \times D^4} = \left(-\frac{\partial P}{\partial z}\right) \text{ Or} \quad (12)$$

$$\frac{Q \times \mu}{3141.3343 \times r^4} = \left(-\frac{\partial P}{\partial z}\right) \text{ mmHg/cm}$$

And $$\gamma = \frac{r}{2 \times \mu \times 0.01} \frac{\text{cm}}{\text{gm/cm-sec}} \left(-\frac{\partial P}{\partial z}\right) \times 1333.22368 \frac{gm}{\text{cm-sec}^2} \frac{1}{\text{cm}}$$

Giving $$\gamma = 66661.1842 \frac{r}{\mu} \left(-\frac{\partial P}{\partial z}\right) \text{sec}^{-1} \quad (13)$$

The maximum velocity is, using equation (12), $$V_{max} = \frac{2 \times 1000}{60 \pi r^2} \times \frac{3141.3343 r^4}{\mu} \left(-\frac{\partial P}{\partial z}\right) \quad (14)$$

$$V_{max} = 33330.6 \frac{r^2}{\mu} \left(-\frac{\partial P}{\partial z}\right) \text{ cm/sec}$$

For eccentric annulus flow, the theoretical formula for eccentric annulus flow is given by White (Viscous Fluid Flow, 1974, McGraw-Hill, ISBN 0-07-069710, equation 3.50) and is reproduced here. The flow rate Q is:

$$Q = \frac{\pi}{8\mu}\left(-\frac{\partial P}{\partial z}\right)\left[a^4 - b^4 - \frac{4c^2 M^2}{\beta - \alpha} - 8c^2 M^2 \sum_{n=1}^{\infty} \frac{ne^{-n(\beta+\alpha)}}{\sinh(n\beta - n\alpha)}\right]$$

where $$M = (F^2 - a^2)^{1/2}$$

$$F = \frac{a^2 - b^2 + c^2}{2c}$$

$$\alpha = \frac{1}{2} \ln \frac{F+M}{F-M}$$

$$\beta = \frac{1}{2} \ln \frac{F-c+M}{F-c-M}$$

and a is equal to $R_2$ 54, b is equal to $R_1$ 52 in the other equations.

Note that in this equation, when b=0 then c=a, giving M=0. This is reduced to the Poiseulle equation. The resultant constant in the equation is same as in (12) above, so the flow rate is:

$$Q = \frac{3141.3343}{\mu} \quad (15)$$

$$\left(-\frac{\partial P}{\partial z}\right)\left[a^4 - b^4 - \frac{4c^2 M^2}{\beta - \alpha} - 8c^2 M^2 \sum_{n=1}^{\infty} \frac{ne^{-n(\beta+\alpha)}}{\sinh(n\beta - n\alpha)}\right] l/\text{min}$$

Q can be expressed in non-dimensional form as well if divide Q by corresponding Poiseulle flow $Q_{ref}$ and let $a=a'R_2$, $b=b'R_2$, $c=c'R_2$, $M=M'R_2^2$. This gives:

$$Q_{nd} = \frac{\frac{\pi}{8\mu}\left(-\frac{\partial P}{\partial z}\right)}{\frac{\pi R_2^4}{8\mu}\left(-\frac{\partial P}{\partial z}\right)}$$

$$\left[a'^4 R_2^4 - b'^4 R_2^4 - \frac{4c'^2 R_2^2 M'^2 R_2^2}{\beta - \alpha} 8c'^2 R_2^2 M'^2 R_2^2 \sum_{n=1}^{\infty} \frac{ne^{-n(\beta+\alpha)}}{\sinh(n\beta - n\alpha)}\right]$$

or $$Q_{nd} = \left[a'^4 - b'^4 - \frac{4c'^2 M'^2}{\beta - \alpha} - 8c'^2 M'^2 \sum_{n=1}^{\infty} \frac{ne^{-n(\beta+\alpha)}}{\sinh(n\beta - n\alpha)}\right]$$

Since $Q_{nd}$ is obtained by normalizing to $Q_{ref}$, the relation to $Q^*$ is $Q^* = \pi Q_{nd}$ as the limiting value of $Q_{nd}$ is 1.

This document also provides methods for implanting a multi-lumen cannula into the heart of a mammal. In some cases, a distal end of the outflow lumen can be positioned a blood vessel, such as the pulmonary artery or the aorta. In some cases, distal end of the inflow lumen can be positioned in a chamber of the heart, such as the left ventricle or the right atrium.

For example, when used with LVADs, the distal region of a cannula can be inserted through a single puncture site in the lowest superficial part of the heart (apex) and extended across the aortic valve. Puncturing the apex of heart can be accomplished by any appropriate method (e.g., cannulation, incision, or excision of the myocardium). In some cases, a cannula can be positioned such that the distal end of the second lumen is in the left ventricle and the distal end of the first lumen is in the aorta. A cannula provided herein can be connected to a heart by anastomosis. For, example, once the cannula is in the desired position in the heart, the cannula can be secured to the myocardium with sutures. A similar arrangement can be used for right heart support.

Figure 5:
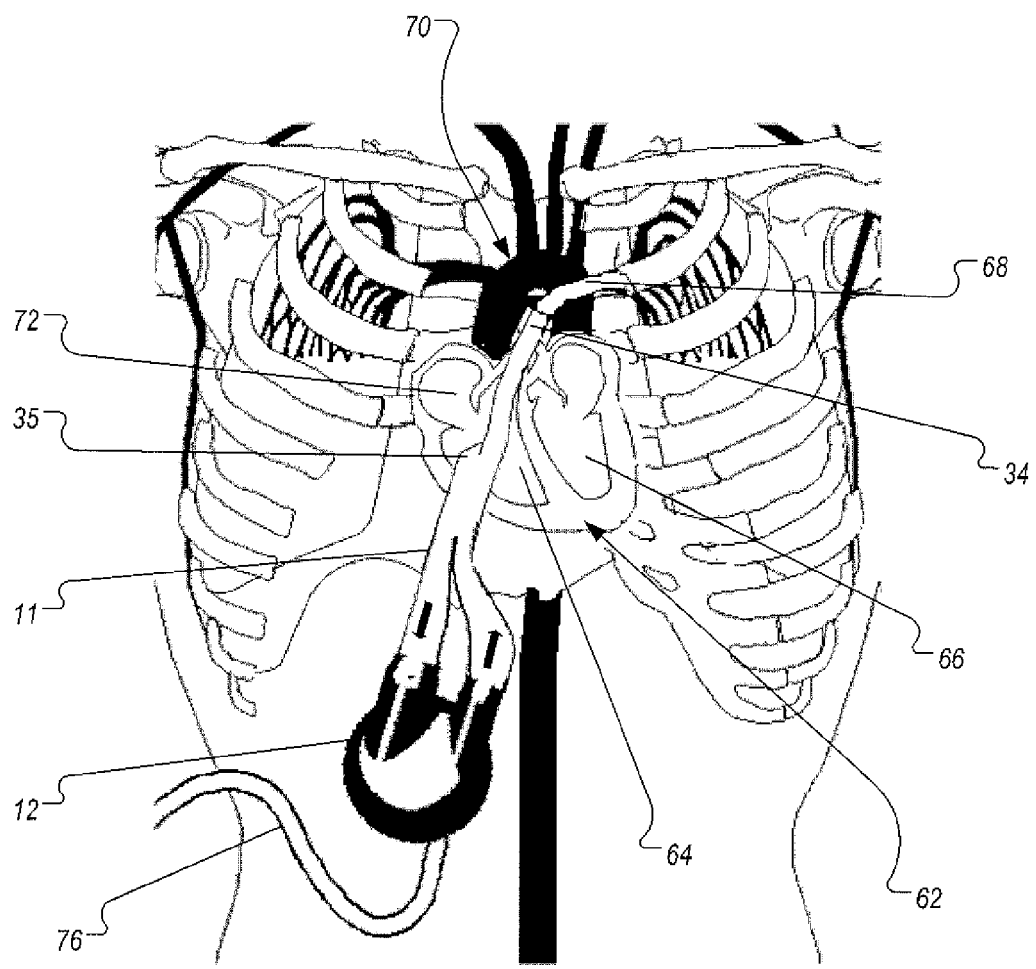
FIG. 5 is a representation of an implanted pump with a cannula inserted in the right ventricle of a person.

Referring to an example implementation shown in FIG. 5, cannula 11 can be inserted into the cardiovascular system, for providing right-side support to a recipient's heart 62 in conjunction with pump 12. For example, cannula 11 can provide an inflow path for blood from a recipient's right ventricle 64 and an outflow path for blood exiting pump 12 to the pulmonary artery 68. In some cases, pump 12 can be placed in the abdominal cavity of a recipient, and be connected to an external power supply by drive-line 76. Of course, although not shown in FIG. 5, the cannula 11 also may be inserted to provide left-side support to the heart 62 (e.g., so that blood from the left ventricle is directed to the blood pump, and pumped into the aorta).

Other configurations for surgical placement of a multi-lumen cannula can be utilized. For example, a multi-lumen cannula can be placed from a peripheral artery by crossing the aortic valve in a retrograde fashion. In some cases, right ventricle support can be similarly achieved by passing a cannula across both right-sided valves in an antigrade fashion. In some cases, a transceptal approach can be utilized by positioning the distal end of the second lumen in the left atrium or left ventricle and the distal end of the first lumen in the aorta.

The invention will be further described in the following examples, which do not limit the scope of the invention described in the claims.

EXAMPLES

Example 1

Flow Characteristics

The flow characteristics for the geometry described in FIG. 4 have been computed in a non-dimensionalized form and converted to dimensional values in general range of those expected for pumping blood. Using the configuration presented in FIG. 4, with radius 52, $R_1$=0.3125 cm, and angle 60, $\alpha$=80°, the pressure gradient was expressed in mmHg/cm, viscosity in cP, flow rate in l/min, velocity in cm/sec and all dimensional measures in cm, $cm^2$. The pressure gradient per unit length may be selected arbitrarily and the results can be linearly scaled to match the capacity of the blood pump and physiologic configuration appropriately.

Where viscosity μ=4 cP
Pressure gradient $\partial P/\partial z$=0.01 mmHG/cm
$R_2$ 54=0.5 cm The non-dimensional values were calculated using numerical methods such as finite element method, and the actual values for lumen 37 were determined to be:

$$\text{Flow rate} = 0.42383 \times 999.7178 \times \frac{0.5^4}{4} \times 0.01 = 0.0662 \; l/\text{min}$$

$$\text{Maximum wall shear rate} = 3.24401 \times 16665.296 \times \frac{0.5}{4} \times 0.01$$
$$= 67.6 \; \text{sec}^{-1}$$

$$\text{Minimum wall shear rate} = 0.85740 \times 16665.296 \times \frac{0.5}{4} \times 0.01$$
$$= 17.9 \; \text{sec}^{-1}$$

$$\text{Maximum flow velocity} = 0.52475 \times 16665.296 \times \frac{0.5^2}{4} \times 0.01$$
$$= 5.5 \; \text{cm/sec}$$

$$\text{Cross sectional area} = 1.69483 \times 0.5^2 = 0.424 \; cm^2$$

The corresponding lumen 36 data were, using equations 12 to 14:

$$\text{Flow rate} = \frac{3141.334 \times 0.3125^4}{4} \times 0.01 = 0.075 \; l/\text{min}$$

$$\text{Wall shear rate} = 66661.1842 \times \frac{0.3125}{4} \times 0.01 = 52 \; \text{sec}^{-1}$$

$$\text{Maximum flow velocity} = 33330.6 \times \frac{0.3125^2}{4} \times 0.01$$
$$= 8.14 \; \text{cm/sec}$$

$$\text{Cross sectional area} = \pi \times 0.3125^2 = 0.307 \; cm^2$$

The actual values were calculated for different configurations of lumens 36 and 37 to determine the relationship of changes in lumen geometry to flow rate, wall shear rate, velocity and total pressure gradient.

The data for flow rate are tabulated in table 2, with $R_2$=1. These data show that flow rate increased asymptotically, and that the increase was insignificant when α60 is greater than 90°. This was determined to be a product of the small increase in cross sectional area and low flow velocity in that area of the cannula. The flow rate decreased asymptotically towards zero as $R_1$ 52 increased.

TABLE 2

| $R_1$ | Angle α (degree) | | | | | | | | | | |
|---|---|---|---|---|---|---|---|---|---|---|---|
| | 40 | 50 | 60 | 70 | 80 | 90 | 100 | 110 | 120 | 130 | 140 |
| 0.250 | 2.13310 | 2.19580 | 2.23110 | 2.25050 | 2.26030 | 2.26490 | 2.26720 | 2.26790 | 2.26820 | 2.26830 | 2.26830 |
| 0.275 | 1.98030 | 2.04840 | 2.08730 | 2.10870 | 2.11960 | 2.12500 | 2.12760 | 2.12840 | 2.12880 | 2.12860 | 2.12880 |
| 0.300 | 1.82710 | 1.90010 | 1.94160 | 1.96470 | 1.97690 | 1.98280 | 1.98560 | 1.98670 | 1.98680 | 1.98690 | 1.98700 |
| 0.325 | 1.67608 | 1.75191 | 1.79585 | 1.82047 | 1.83340 | 1.83985 | 1.84283 | 1.84388 | 1.84422 | 1.84432 | 1.84455 |
| 0.350 | 1.52820 | 1.60560 | 1.65117 | 1.67662 | 1.69031 | 1.69740 | 1.70045 | 1.70169 | 1.70214 | 1.70226 | 1.70222 |
| 0.375 | 1.38461 | 1.46237 | 1.50858 | 1.53505 | 1.54928 | 1.55653 | 1.55989 | 1.56121 | 1.56169 | 1.56189 | 1.56184 |
| 0.400 | 1.24653 | 1.32326 | 1.36963 | 1.39656 | 1.41113 | 1.41856 | 1.42203 | 1.42346 | 1.42394 | 1.42411 | 1.42418 |
| 0.425 | 1.11469 | 1.18947 | 1.23534 | 1.26207 | 1.27681 | 1.28430 | 1.28793 | 1.28947 | 1.29000 | 1.29014 | 1.29010 |
| 0.450 | 0.98981 | 1.06162 | 1.10619 | 1.13260 | 1.14725 | 1.15478 | 1.15842 | 1.16003 | 1.16057 | 1.16076 | 1.16072 |
| 0.475 | 0.87240 | 0.94019 | 0.98308 | 1.00882 | 1.02320 | 1.03072 | 1.03427 | 1.03586 | 1.03651 | 1.03664 | 1.03668 |
| 0.500 | 0.76281 | 0.82615 | 0.86677 | 0.89143 | 0.90530 | 0.91266 | 0.91615 | 0.91772 | 0.91835 | 0.91856 | 0.91864 |
| 0.525 | 0.66126 | 0.71970 | 0.75761 | 0.78086 | 0.79416 | 0.80109 | 0.80456 | 0.80624 | 0.80684 | 0.80705 | 0.80704 |
| 0.550 | 0.56785 | 0.62099 | 0.65595 | 0.67753 | 0.69013 | 0.69672 | 0.70005 | 0.70171 | 0.70228 | 0.70240 | 0.70245 |
| 0.575 | 0.48273 | 0.53045 | 0.56209 | 0.58194 | 0.59350 | 0.59974 | 0.60295 | 0.60443 | 0.60502 | 0.60521 | 0.60524 |
| 0.600 | 0.40575 | 0.44790 | 0.47617 | 0.49413 | 0.50475 | 0.51056 | 0.51349 | 0.51481 | 0.51543 | 0.51557 | 0.51567 |
| 0.625 | 0.33682 | 0.37338 | 0.39836 | 0.41431 | 0.42383 | 0.42914 | 0.43181 | 0.43303 | 0.43365 | 0.43377 | 0.43388 |
| 0.650 | 0.27565 | 0.30695 | 0.32851 | 0.34246 | 0.35080 | 0.35557 | 0.35797 | 0.35911 | 0.35964 | 0.35982 | 0.35981 |
| 0.675 | 0.22198 | 0.24826 | 0.26654 | 0.27841 | 0.28579 | 0.28992 | 0.29207 | 0.29306 | 0.29351 | 0.29372 | 0.29369 |
| 0.700 | 0.17551 | 0.19708 | 0.21227 | 0.22225 | 0.22845 | 0.23208 | 0.23390 | 0.23480 | 0.23515 | 0.23533 | 0.23537 |
| 0.725 | 0.13577 | 0.15311 | 0.16543 | 0.17362 | 0.17876 | 0.18179 | 0.18333 | 0.18409 | 0.18435 | 0.18455 | 0.18457 |
| 0.750 | 0.10239 | 0.11594 | 0.12563 | 0.13214 | 0.13631 | 0.13874 | 0.14000 | 0.14064 | 0.14092 | 0.14104 | 0.14107 |
| 0.775 | 0.07488 | 0.08511 | 0.09247 | 0.09751 | 0.10078 | 0.10263 | 0.10367 | 0.10416 | 0.10442 | 0.10450 | 0.10455 |
| 0.800 | 0.05273 | 0.06014 | 0.06553 | 0.06928 | 0.07167 | 0.07310 | 0.07393 | 0.07432 | 0.07447 | 0.07452 | 0.07457 |

The maximum shear rate (Table 3) decreased linearly as $R_1$ 52 increased. The minimum wall shear rate (Table 4) decreased asymptotically towards zero as α60 increased. When $R_3$ 56 decreased towards zero (as α60 increased towards 180) the flow velocity in the region bound by the arc of $R_3$ 56 also decreases to zero. Therefore, the wall shear rate decreased to zero.

TABLE 3

| | Angle α (degree) | | | | | | | | | | |
|---|---|---|---|---|---|---|---|---|---|---|---|
| $R_1$ | 40 | 50 | 60 | 70 | 80 | 90 | 100 | 110 | 120 | 130 | 140 |
| 0.250 | 6.57130 | 6.68910 | 6.94640 | 6.93310 | 6.83720 | 6.92180 | 6.96530 | 6.92200 | 6.97160 | 6.95410 | 6.93730 |
| 0.275 | 6.33170 | 6.52820 | 6.59760 | 6.55530 | 6.61060 | 6.77620 | 6.70590 | 6.70390 | 6.66730 | 6.77580 | 6.67920 |
| 0.300 | 6.04000 | 6.27790 | 6.39480 | 6.40620 | 6.37380 | 6.52200 | 6.46450 | 6.45490 | 6.44030 | 6.53450 | 6.41100 |
| 0.325 | 5.84551 | 6.04709 | 6.14347 | 6.10662 | 6.20206 | 6.18873 | 6.21725 | 6.26717 | 6.18230 | 6.14669 | 6.21901 |
| 0.350 | 5.66895 | 5.83101 | 5.89415 | 5.89114 | 5.96762 | 5.89150 | 5.92645 | 5.87783 | 5.89087 | 5.93102 | 5.96582 |
| 0.375 | 5.45116 | 5.57666 | 5.61381 | 5.74144 | 5.64999 | 5.67678 | 5.70371 | 5.66028 | 5.65532 | 5.67529 | 5.66801 |
| 0.400 | 5.17482 | 5.32309 | 5.39263 | 6.48418 | 5.42821 | 5.41749 | 5.45975 | 5.40620 | 5.38912 | 5.46658 | 5.43339 |
| 0.425 | 4.96221 | 5.11576 | 5.20807 | 5.23654 | 5.15413 | 5.20654 | 5.16295 | 5.16728 | 5.16251 | 5.16992 | 5.15455 |
| 0.450 | 4.74298 | 4.86049 | 4.95581 | 4.91659 | 4.95511 | 4.94617 | 4.91734 | 4.93898 | 4.91290 | 4.93083 | 4.90958 |
| 0.475 | 4.53841 | 4.66292 | 4.66683 | 4.69966 | 4.70253 | 4.69435 | 4.69059 | 4.67150 | 4.68570 | 4.68978 | 4.66700 |
| 0.500 | 4.32062 | 4.42209 | 4.43088 | 4.47055 | 4.44652 | 4.46382 | 4.43656 | 4.45218 | 4.45053 | 4.45225 | 4.46200 |
| 0.525 | 4.10839 | 4.18325 | 4.18537 | 4.20610 | 4.22287 | 4.20109 | 4.20740 | 4.21911 | 4.21652 | 4.22435 | 4.20678 |
| 0.550 | 3.86883 | 3.91672 | 3.93953 | 3.97136 | 3.97282 | 3.97263 | 3.96551 | 3.99208 | 3.97561 | 3.94352 | 3.98792 |
| 0.575 | 3.64810 | 3.70817 | 3.71502 | 3.72443 | 3.72993 | 3.72358 | 3.72921 | 3.71925 | 3.70600 | 3.73639 | 3.72447 |
| 0.600 | 3.41940 | 3.49302 | 3.42364 | 3.47994 | 3.47462 | 3.49419 | 3.48305 | 3.50749 | 3.50765 | 3.48362 | 3.47092 |
| 0.625 | 3.21533 | 3.23356 | 3.21538 | 3.20698 | 3.24401 | 3.24110 | 3.19194 | 3.20103 | 3.26088 | 3.23870 | 3.24760 |
| 0.650 | 2.97994 | 2.95760 | 2.95990 | 2.98417 | 2.96070 | 2.96950 | 2.97194 | 3.00872 | 2.97904 | 2.97086 | 2.98150 |
| 0.675 | 2.72063 | 2.74334 | 2.78358 | 2.75232 | 2.74335 | 2.74414 | 2.75337 | 2.77350 | 2.73652 | 2.74651 | 2.76404 |
| 0.700 | 2.53872 | 2.52008 | 2.51784 | 2.54512 | 2.53893 | 2.53395 | 2.54593 | 2.54784 | 2.53485 | 2.52988 | 2.51605 |
| 0.725 | 2.29594 | 2.30174 | 2.30170 | 2.29923 | 2.31077 | 2.31419 | 2.30718 | 2.31854 | 2.30629 | 2.30954 | 2.31481 |
| 0.750 | 2.07188 | 2.08666 | 2.08776 | 2.08728 | 2.08671 | 2.07885 | 2.09260 | 2.09292 | 2.09083 | 2.08274 | 2.09073 |
| 0.775 | 1.87483 | 1.86542 | 1.86361 | 1.84379 | 1.85891 | 1.85818 | 1.88397 | 1.85859 | 1.86914 | 1.85212 | 1.86362 |
| 0.800 | 1.64411 | 1.64434 | 1.61839 | 1.62330 | 1.59794 | 1.62635 | 1.63324 | 1.63680 | 1.65552 | 1.58783 | 1.61462 |

TABLE 4

| | Angle α (degree) | | | | | | | | | | |
|---|---|---|---|---|---|---|---|---|---|---|---|
| $R_1$ | 40 | 50 | 60 | 70 | 80 | 90 | 100 | 110 | 120 | 130 | 140 |
| 0.250 | 2.67750 | 2.42100 | 2.12910 | 1.81230 | 1.49010 | 1.16530 | 0.86129 | 0.59640 | 0.38310 | 0.22764 | 0.12672 |
| 0.275 | 2.61570 | 2.36500 | 2.08320 | 1.77550 | 1.45680 | 1.14370 | 0.85226 | 0.59367 | 0.38720 | 0.23372 | 0.13137 |
| 0.300 | 2.54320 | 2.29400 | 2.03250 | 1.72670 | 1.42330 | 1.12280 | 0.83804 | 0.59022 | 0.38824 | 0.23868 | 0.13680 |
| 0.325 | 2.47399 | 2.23412 | 1.97826 | 1.68007 | 1.38501 | 1.10102 | 0.82374 | 0.58309 | 0.38968 | 0.24304 | 0.13981 |
| 0.350 | 2.39937 | 2.17399 | 1.91828 | 1.63875 | 1.35237 | 1.07470 | 0.80903 | 0.57624 | 0.38914 | 0.24545 | 0.14311 |
| 0.375 | 2.32136 | 2.10653 | 1.85789 | 1.58804 | 1.31309 | 1.04207 | 0.79123 | 0.57072 | 0.38701 | 0.24663 | 0.14531 |
| 0.400 | 2.24459 | 2.02869 | 1.79561 | 1.53655 | 1.27326 | 1.01105 | 0.77581 | 0.56105 | 0.38541 | 0.24746 | 0.14785 |
| 0.425 | 2.16124 | 1.96242 | 1.73468 | 1.48764 | 1.23191 | 0.98598 | 0.75688 | 0.55261 | 0.38026 | 0.24609 | 0.14786 |
| 0.450 | 2.08042 | 1.88661 | 1.66496 | 1.43553 | 1.18850 | 0.95490 | 0.73694 | 0.53921 | 0.37668 | 0.24562 | 0.14819 |
| 0.475 | 1.97856 | 1.81131 | 1.60025 | 1.37215 | 1.14431 | 0.91724 | 0.71551 | 0.52683 | 0.37037 | 0.24372 | 0.14788 |
| 0.500 | 1.90034 | 1.72797 | 1.53543 | 1.32912 | 1.10169 | 0.88145 | 0.69643 | 0.51347 | 0.36029 | 0.24076 | 0.14775 |
| 0.525 | 1.81358 | 1.65407 | 1.46396 | 1.25620 | 1.06201 | 0.85027 | 0.66734 | 0.49688 | 0.35170 | 0.23645 | 0.14558 |
| 0.550 | 1.71489 | 1.56912 | 1.39270 | 1.19935 | 1.00575 | 0.81053 | 0.64458 | 0.48123 | 0.34380 | 0.23132 | 0.14350 |
| 0.575 | 1.63077 | 1.48768 | 1.31922 | 1.14336 | 0.96022 | 0.77133 | 0.61670 | 0.46341 | 0.33313 | 0.22452 | 0.14043 |
| 0.600 | 1.53832 | 1.40143 | 1.24236 | 1.07617 | 0.91018 | 0.74965 | 0.58632 | 0.44389 | 0.31969 | 0.21817 | 0.13628 |
| 0.625 | 1.44474 | 1.31505 | 1.16949 | 1.01367 | 0.85740 | 0.70376 | 0.56073 | 0.42377 | 0.30893 | 0.21079 | 0.13229 |
| 0.650 | 1.34688 | 1.22989 | 1.09583 | 0.95002 | 0.80474 | 0.66767 | 0.52945 | 0.40544 | 0.29302 | 0.20195 | 0.12697 |
| 0.675 | 1.24980 | 1.14066 | 1.01886 | 0.89847 | 0.76096 | 0.62665 | 0.49851 | 0.38186 | 0.27822 | 0.19282 | 0.12183 |
| 0.700 | 1.15205 | 1.05395 | 0.94618 | 0.82121 | 0.70183 | 0.58637 | 0.46819 | 0.36001 | 0.26457 | 0.18183 | 0.11589 |
| 0.725 | 1.06695 | 0.95985 | 0.86899 | 0.76311 | 0.65554 | 0.54298 | 0.43531 | 0.33593 | 0.24719 | 0.17068 | 0.10880 |
| 0.750 | 0.95919 | 0.88016 | 0.78639 | 0.68639 | 0.59748 | 0.49300 | 0.39905 | 0.30942 | 0.22837 | 0.15833 | 0.10205 |
| 0.775 | 0.85579 | 0.78705 | 0.70261 | 0.61881 | 0.54105 | 0.45283 | 0.36509 | 0.28271 | 0.21041 | 0.14649 | 0.09400 |
| 0.800 | 0.76510 | 0.70664 | 0.62494 | 0.56082 | 0.48244 | 0.40539 | 0.32858 | 0.25609 | 0.19017 | 0.13345 | 0.08550 |

The maximum velocity (Table 5) did not vary significantly with angle α60, decreasing almost linearly as $R_1$ 52 increased.

TABLE 5

| | Angle α (degree) | | | | | | | | | | |
|---|---|---|---|---|---|---|---|---|---|---|---|
| $R_1$ | 40 | 50 | 60 | 70 | 80 | 90 | 100 | 110 | 120 | 130 | 140 |
| 0.250 | 1.59580 | 1.61260 | 1.62120 | 1.62540 | 1.62740 | 1.62800 | 1.62830 | 1.62820 | 1.62830 | 1.62840 | 1.62840 |
| 0.275 | 1.52690 | 1.54460 | 1.55350 | 1.55760 | 1.55960 | 1.56030 | 1.56070 | 1.56060 | 1.56070 | 1.56070 | 1.56080 |

TABLE 5-continued

| $R_1$ | 40 | 50 | 60 | 70 | 80 | 90 | 100 | 110 | 120 | 130 | 140 |
|---|---|---|---|---|---|---|---|---|---|---|---|
| 0.300 | 1.45520 | 1.47380 | 1.48280 | 1.48710 | 1.48890 | 1.48950 | 1.49010 | 1.48990 | 1.48990 | 1.48980 | 1.49000 |
| 0.325 | 1.38187 | 1.40066 | 1.40966 | 1.41406 | 1.41566 | 1.41628 | 1.41686 | 1.41684 | 1.41669 | 1.41675 | 1.41685 |
| 0.350 | 1.30762 | 1.32626 | 1.33532 | 1.33909 | 1.34066 | 1.34140 | 1.34151 | 1.34175 | 1.34153 | 1.34165 | 1.34175 |
| 0.375 | 1.23271 | 1.25050 | 1.25892 | 1.26294 | 1.26438 | 1.26496 | 1.26510 | 1.26528 | 1.26520 | 1.26535 | 1.26507 |
| 0.400 | 1.15718 | 1.17418 | 1.18224 | 1.18572 | 1.18725 | 1.18776 | 1.18789 | 1.18796 | 1.18784 | 1.18802 | 1.18802 |
| 0.425 | 1.08181 | 1.09777 | 1.10522 | 1.10828 | 1.10965 | 1.10994 | 1.10998 | 1.11017 | 1.11011 | 1.11028 | 1.11025 |
| 0.450 | 1.00674 | 1.02154 | 1.02816 | 1.03098 | 1.03213 | 1.03229 | 1.03263 | 1.03260 | 1.03252 | 1.03260 | 1.03267 |
| 0.475 | 0.93256 | 0.94562 | 0.95169 | 0.95420 | 0.95519 | 0.95546 | 0.95555 | 0.95551 | 0.95555 | 0.95540 | 0.95535 |
| 0.500 | 0.85912 | 0.87085 | 0.87614 | 0.87827 | 0.87908 | 0.87922 | 0.87922 | 0.87916 | 0.87931 | 0.87931 | 0.87927 |
| 0.525 | 0.78721 | 0.79767 | 0.80207 | 0.80347 | 0.80406 | 0.80425 | 0.80440 | 0.80446 | 0.80453 | 0.80442 | 0.80444 |
| 0.550 | 0.71674 | 0.72549 | 0.72928 | 0.73066 | 0.73099 | 0.73118 | 0.73114 | 0.73109 | 0.73119 | 0.73115 | 0.73098 |
| 0.575 | 0.64826 | 0.65587 | 0.65827 | 0.65957 | 0.65976 | 0.65974 | 0.65988 | 0.66004 | 0.65997 | 0.65997 | 0.66000 |
| 0.600 | 0.58185 | 0.58788 | 0.59000 | 0.59084 | 0.59125 | 0.59116 | 0.59112 | 0.59098 | 0.59109 | 0.59096 | 0.59109 |
| 0.625 | 0.51788 | 0.52246 | 0.52416 | 0.52472 | 0.52475 | 0.52492 | 0.52474 | 0.52469 | 0.52490 | 0.52485 | 0.52479 |
| 0.650 | 0.45641 | 0.45985 | 0.46121 | 0.46147 | 0.46134 | 0.46160 | 0.46145 | 0.46151 | 0.46141 | 0.46159 | 0.46146 |
| 0.675 | 0.39788 | 0.40039 | 0.40111 | 0.40144 | 0.40129 | 0.40152 | 0.40150 | 0.40137 | 0.40137 | 0.40141 | 0.40135 |
| 0.700 | 0.34231 | 0.34464 | 0.34485 | 0.34486 | 0.34485 | 0.34488 | 0.34471 | 0.34476 | 0.34483 | 0.34468 |
| 0.725 | 0.29030 | 0.29143 | 0.29175 | 0.29180 | 0.29187 | 0.29180 | 0.29171 | 0.29182 | 0.29186 | 0.29181 | 0.29189 |
| 0.750 | 0.24191 | 0.24260 | 0.24275 | 0.24268 | 0.24266 | 0.24290 | 0.24278 | 0.24279 | 0.24275 | 0.24292 | 0.24272 |
| 0.775 | 0.19733 | 0.19777 | 0.19774 | 0.19779 | 0.19786 | 0.19775 | 0.19777 | 0.19777 | 0.19776 | 0.19771 | 0.19779 |
| 0.800 | 0.15689 | 0.15705 | 0.15712 | 0.15710 | 0.15687 | 0.15687 | 0.15707 | 0.15704 | 0.15713 | 0.15714 | 0.15702 |

Example 2

Pressure Gradient Determination

A possible minimal pressure gradient for a cannula as provided herein was determined as follows. The pressure gradients for return flow through lumens 36 and 37 were calculated for different values of angle α 60 and $R_1$ 52 (Table 6). The minimum pressure gradient occurred at $R_2$=1.0, $R_1 \approx 0.6$ to 0.625 and angle $\alpha \approx 90°$.

TABLE 6

| $R_1$ | 40 | 50 | 60 | 70 | 80 | 90 | 100 | 110 | 120 | 130 | 140 |
|---|---|---|---|---|---|---|---|---|---|---|---|
| 0.250 | 0.3279 | 0.3278 | 0.3278 | 0.3278 | 0.3277 | 0.3277 | 0.3277 | 0.3277 | 0.3277 | 0.3277 | 0.3277 |
| 0.275 | 0.2247 | 0.2246 | 0.2246 | 0.2245 | 0.2245 | 0.2245 | 0.2245 | 0.2245 | 0.2245 | 0.2245 | 0.2245 |
| 0.300 | 0.1594 | 0.1593 | 0.1593 | 0.1592 | 0.1592 | 0.1592 | 0.1592 | 0.1592 | 0.1592 | 0.1592 | 0.1592 |
| 0.325 | 0.1165 | 0.1164 | 0.1164 | 0.1163 | 0.1163 | 0.1163 | 0.1163 | 0.1163 | 0.1163 | 0.1163 | 0.1163 |
| 0.350 | 0.0875 | 0.0873 | 0.0873 | 0.0872 | 0.0872 | 0.0872 | 0.0872 | 0.0872 | 0.0872 | 0.0872 | 0.0872 |
| 0.375 | 0.0673 | 0.0671 | 0.0670 | 0.0670 | 0.0670 | 0.0670 | 0.0670 | 0.0670 | 0.0670 | 0.0670 | 0.0670 |
| 0.400 | 0.0529 | 0.0528 | 0.0527 | 0.0526 | 0.0526 | 0.0526 | 0.0526 | 0.0526 | 0.0525 | 0.0525 | 0.0525 |
| 0.425 | 0.0426 | 0.0424 | 0.0423 | 0.0422 | 0.0422 | 0.0421 | 0.0421 | 0.0421 | 0.0421 | 0.0421 | 0.0421 |
| 0.450 | 0.0351 | 0.0348 | 0.0347 | 0.0346 | 0.0345 | 0.0345 | 0.0345 | 0.0345 | 0.0345 | 0.0345 | 0.0345 |
| 0.475 | 0.0296 | 0.0293 | 0.0291 | 0.0290 | 0.0289 | 0.0289 | 0.0289 | 0.0289 | 0.0289 | 0.0289 | 0.0289 |
| 0.500 | 0.0256 | 0.0252 | 0.0250 | 0.0249 | 0.0248 | 0.0248 | 0.0247 | 0.0247 | 0.0247 | 0.0247 | 0.0247 |
| 0.525 | 0.0228 | 0.0223 | 0.0220 | 0.0219 | 0.0218 | 0.0218 | 0.0217 | 0.0217 | 0.0217 | 0.0217 | 0.0217 |
| 0.550 | 0.0210 | 0.0204 | 0.0200 | 0.0198 | 0.0197 | 0.0197 | 0.0196 | 0.0196 | 0.0196 | 0.0196 | 0.0196 |
| 0.575 | 0.0199 | 0.0192 | 0.0188 | 0.0185 | 0.0184 | 0.0183 | 0.0183 | 0.0183 | 0.0183 | 0.0183 | 0.0183 |
| 0.600 | 0.0197 | 0.0188 | 0.0182 | 0.0179 | 0.0178 | 0.0177 | 0.0176 | 0.0176 | 0.0176 | 0.0176 | 0.0176 |
| 0.625 | 0.0202 | 0.0191 | 0.0184 | 0.0180 | 0.0178 | 0.0177 | 0.0176 | 0.0176 | 0.0176 | 0.0176 | 0.0176 |
| 0.650 | 0.0216 | 0.0202 | 0.0193 | 0.0188 | 0.0185 | 0.0184 | 0.0183 | 0.0183 | 0.0183 | 0.0183 | 0.0183 |
| 0.675 | 0.0242 | 0.0223 | 0.0211 | 0.0205 | 0.0201 | 0.0199 | 0.0198 | 0.0198 | 0.0198 | 0.0198 | 0.0198 |
| 0.700 | 0.0281 | 0.0256 | 0.0242 | 0.0233 | 0.0228 | 0.0225 | 0.0224 | 0.0223 | 0.0223 | 0.0223 | 0.0223 |
| 0.725 | 0.0341 | 0.0307 | 0.0288 | 0.0277 | 0.0270 | 0.0266 | 0.0264 | 0.0263 | 0.0263 | 0.0263 | 0.0263 |
| 0.750 | 0.0431 | 0.0385 | 0.0359 | 0.0343 | 0.0334 | 0.0329 | 0.0326 | 0.0325 | 0.0324 | 0.0324 | 0.0324 |
| 0.775 | 0.0570 | 0.0505 | 0.0468 | 0.0446 | 0.0432 | 0.0425 | 0.0421 | 0.0419 | 0.0418 | 0.0418 | 0.0418 |
| 0.800 | 0.0790 | 0.0696 | 0.0642 | 0.0609 | 0.0589 | 0.0578 | 0.0572 | 0.0569 | 0.0568 | 0.0568 | 0.0568 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for implanting a cannula into a cardiovascular system, the method comprising:
   creating a single puncture site into the cardiovascular system for receiving the cannula;
   inserting the cannula through the puncture site such that a distal end of a first lumen of the cannula and a distal end of a second lumen of the cannula pass through the puncture site into the cardiovascular system, the second lumen having a non-circular cross-sectional shape extending between a first end portion and a second end portion, the first and second end portions having rounded corners each with a radius greater than about ten percent of the radius of the largest circle that can be inscribed within the second lumen and less than the radius of the largest circle that can be inscribed within the second lumen;

positioning the distal end of the first lumen of the cannula within a first portion of the cardiovascular system; and positioning the distal end of the second lumen of the cannula within a second portion of the cardiovascular system, such that in use blood is received in the cannula from the distal end of the second lumen and blood is pumped from the cannula through the distal end of the first lumen having a cross-sectional area smaller than the cross-sectional area of the second lumen.

2. The method of claim 1, wherein the distal end of the second lumen is positioned in the left ventricle or the left atrium, and wherein the distal end of the first lumen is positioned in the aorta.

3. The method of claim 2, wherein the single puncture site is at the apex of the heart.

4. The method of claim 1, further comprising connecting a blood pump to a proximal region of the cannula, the proximal region of the cannula comprising proximal ends of the first and second lumens.

5. The method of claim 4, further comprising placing the blood pump in the abdominal cavity.

6. The method of claim 1, wherein the single puncture site is into the heart, the method further comprising connecting the cannula to the heart by anastomosis.

7. The method of claim 6, wherein once the cannula is positioned at a desired configuration relative to the heart, the cannula is secured to the myocardium using sutures.

8. The method of claim 1, wherein inserting the cannula comprises inserting the cannula through a septum of the heart.

9. The method of claim 8, wherein the distal end of the second lumen is positioned in the left ventricle or the left atrium, and wherein the distal end of the first lumen is positioned in the aorta.

10. The method of claim 1, wherein the distal end of the second lumen is positioned in the right ventricle or the right atrium, and wherein the distal end of the first is positioned in the pulmonary artery.

11. The method of claim 1, wherein creating the single puncture site into the cardiovascular system is accomplished by cannulation, incision, or excision of the myocardium.

12. The method of claim 1, wherein the distal end of the second lumen is positioned in the heart, and wherein the distal end of the first lumen is positioned in a blood vessel.

13. The method of claim 1, wherein the cross-sectional area of the first lumen and the second lumen is about 93% of the cross-sectional area of the cannula.

14. The method of claim 1, wherein the cross-sectional areas of the first lumen and the second lumen are substantially maintained during use.

15. The method of claim 1, wherein the distal end of the first lumen is sufficiently flexible to permit manipulation within the cardiovascular system, and wherein the distal end of the second lumen is rigid.

16. The method of claim 1, wherein the cross-sectional shape of the second lumen comprises a reniform shape.

17. A cannula for use with a blood pump, the cannula comprising:

a housing having a proximal region, a distal region, and an intermediate region located between the proximal and distal regions, wherein the housing defines a first lumen and a second lumen, wherein the first lumen comprises:
(a) a proximal end located at or near the proximal region of the housing and adapted to engage the blood pump, and
(b) a distal end located at or near the distal region of the housing and adapted to be positioned within a cardiovascular system, wherein the second lumen comprises:
(a) a proximal end located at or near the proximal region of the housing and adapted to engage the blood pump, and
(b) a distal end located at or near the intermediate region of the housing and adapted to be positioned within the cardiovascular system, wherein one of the first and second lumens has a cross-sectional shape extending between a first end portion and a second end portion, the first and second end portions having rounded corners each with a radius greater than about ten percent of the radius of the largest circle that can be inscribed within the one of the first and second lumens and less than the radius of the largest circle that can be inscribed within the one of the first and second lumens, such lumen with rounded corners being off-set from the geometric center of the other lumen.

18. The cannula of claim 17, wherein the one of the first and second lumens comprises the second lumen.

19. The cannula of claim 18, wherein the cross-sectional shape of the second lumen comprises a reniform shape.

20. The cannula of claim 17, wherein the distal end of the first lumen is sufficiently flexible to permit manipulation within the cardiovascular system, and wherein the distal end of the second lumen is rigid.

21. The cannula of claim 17, wherein the first and second lumens are separated by a septum having a concave surface on one side to define a portion of the first lumen and a convex surface on an opposite side to define a portion of the second lumen.

* * * * *